United States Patent [19]

Cullinan

[11] Patent Number: 5,545,661
[45] Date of Patent: Aug. 13, 1996

[54] METHODS FOR INHIBITING BONE LOSS WITH BIS-PYRONE OXOVANADIUM COMPOUNDS

[75] Inventor: George J. Cullinan, Trafalgar, Ind.

[73] Assignee: Eli Lilly and Company, Indianapolis, Ind.

[21] Appl. No.: 442,456

[22] Filed: May 16, 1995

[51] Int. Cl.$^6$ ...................................................... A61K 31/35
[52] U.S. Cl. ........................... 514/460; 514/449; 514/456
[58] Field of Search .................................... 514/449, 456, 514/460

[56] References Cited

FOREIGN PATENT DOCUMENTS

WO93/06811  4/1993  WIPO.

OTHER PUBLICATIONS

Dai, S., et al., *Pharmacology Communications*, 3(4):311–321 (1993).
Dai, S., et al., *Pharmacology & Toxicology*, 75:265–273 (1994).
McNeil, J. H., et al., *J. Med. Chem.*, 35(8):1489–1491 (1992).
Stinson, R. A., et al., *Clinica Chimica Acta*, 110:261–272 (1981).
Krieger, N. S., et al., *Endocrinology*, 113(1):324–328 (1983).

Primary Examiner—Theodore J. Criares
Attorney, Agent, or Firm—James P. Leeds; David E. Boone

[57] ABSTRACT

The present invention provides a method for inhibiting bone loss comprising administering to a human in need of treatment an effective amount of a compound of formula I

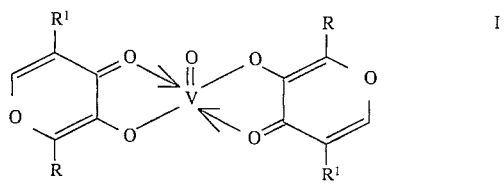

wherein
each R is the same or different —H, —$C_1$-$C_6$ alkyl, —$CH_2OH$, or —$CH_2O(C_1$-$C_6)$ alkyl; and
each $R^1$ is the same or different —H, —$C_1$-$C_6$ alkyl, —$CH_2OH$, or —$CH_2O(C_1$-$C_6)$alkyl;
or a pharmaceutically acceptable solvate or hydrate thereof, and pharmaceutical compositions thereof.

11 Claims, No Drawings

METHODS FOR INHIBITING BONE LOSS WITH BIS-PYRONE OXOVANADIUM COMPOUNDS

FIELD OF THE INVENTION

The present invention relates to the fields of pharmacology and pharmaceutical chemistry, and provides methods for inhibiting the loss of bone in humans.

BACKGROUND OF THE INVENTION

The mechanism of bone loss is not well understood, but in practical effect, the disorder arises from an imbalance in the formation of new healthy bone and the resorption of old bone, skewed toward a net loss of bone tissue. This bone loss includes a decrease in both mineral content and protein matrix components of the bone, and leads to an increased fracture rate of, predominantly, femoral bones and bones in the forearm and vertebrae. These fractures, in turn, lead to an increase in general morbidity, a marked loss of stature and mobility, and, in many cases, an increase in mortality resulting from complications.

Bone loss occurs in a wide range of subjects including postmenopausal women, patients who have undergone hysterectomy, patients who are undergoing or have undergone long-term administration of corticosteroids, patients suffering from Cushing's syndrome, and patents having gonadal dysgenesis.

Unchecked bone loss can lead to osteoporosis which describes a group of diseases which arise from diverse etiologies. The consequence of this loss of bone mass and resulting bone fracture is the failure of the skeleton to provide adequate structural support for the body.

Two of the most common types of osteoporosis are Postmenopausal and senile osteoporosis.

Postmenopausal Osteoporosis

One of the most common types of osteoporosis is that associated with menopause. Most women lose between 20–60% of the bone mass in the trabecular compartment of the bone within 3–6 years after the cessation of menses. This rapid loss is generally associated with an increase of bone resorption and formation. However, the resorptive cycle is more dominant and the result is a net loss of bone mass.

Osteoporosis is a common and serious disease among postmenopausal women. There are an estimated 25 million women in the United States alone, who are afflicted with this disease. The results of osteoporosis are both personally harmful, and also account for a large economic loss due its chronicity and the need for extensive and long-term support (hospitalization and nursing home care) from the disease sequellae. This is especially true in more elderly patients. Additionally, osteoporosis is generally not thought of as a life threatening condition, but a 20–30% mortality rate is related with hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy bone and is particularly concentrated near the ends of the bone near the joints and in the vertebrae of the spine. The trabecular tissue is characterized by small osteoid structures which inter-connect with each other as well as the more solid and dense cortical tissue which makes up the outer surface and central shaft of the bone. This criss-cross network of trabeculae gives lateral support to the outer cortical structure and is critical to the biomechanical strength of the overall structure. In postmenopausal osteoporosis, it is, primarily, the net resorption and loss of the trabeculae which leads to the failure and fracture of the bone. In light of the loss of the trabeculae in postmenopausal women, it is not surprising that the most common fractures are those associated with bones which are highly dependent on trabecular support, e.g., the vertebrae, the neck of the weight bearing bones (femur) and the forearm. Indeed, hip fracture, collies fractures, and vetebral crush fractures are indicative of postmenopausal osteoporosis.

Presently, the only generally accepted method for the treatment for post menopausal osteoporosis is estrogen replacement therapy. Although this therapy frequently is successful, patient compliance is low, primarily due to the undesirable side-effects of estrogen treatment. Frequently cited side-effects of estrogen replacement therapy include reinitiation of menses, bloating, depression, and fear of breast or uterine cancer. In order to limit the known threat of uterine cancer in those women who have not undergone a hysterectomy, a protocol of estrogen and progestin cyclic therapy is often employed. This protocol is similar to that which is used in birth control regimens, and often is not tolerated by many women because of the side-effects characteristic of progestin.

More recently, certain antiestrogens, originally developed for the treatment of breast cancer, have been shown in experimental models of postmenopausal osteoporosis to be efficacious. Among these agents is raloxifene, which is undergoing clinical evaluation [see, e.g., U.S. Pat. No. 5,393,763; and Black, L. J., et al., *J. Clin, Invest.*, 93:63–69 (1994)]. In addition, tamoxifene, a widely used clinical agent for the treatment of breast cancer, has been shown to increase bone mineral density in post menopausal women suffering from breast cancer [Love, R. R., et al., *N. Engl. J. Med.*, 326:852–856 (1992)]. To date, none of the antiestrogens have been approved for use in postmenopausal osteoporosis.

Another therapy for the treatment of postmenopausal osteoporosis is the use of calcitonin. Calcitonin is a naturally occurring peptide which inhibits bone resorption and has been approved for this use in many countries [see, e.g., Overgaard, K., et al., *Br. Med. J.*, 305:556–561 (1992)]. The use of calcitonin has been somewhat limited. Its effects are very modest in increasing bone mineral density and the treatment is very expensive. Equally problematic is the fact that the peptide must be given by parenteral administration.

Another therapy for the treatment of postmenopausal osteoporosis is the use of bis-phosphonates. These compounds were originally developed for use in Paget's disease and malignant hypercalcemia. They have been shown to inhibit the bone resorption activity of osteoclasts. Several compounds of this class are currently undergoing clinical evaluation and several have been approved for the treatment of postmenopausal osteoporosis and include etidronate, alendronate, and pamidronate. These agents may be helpful in the treatment of osteoporosis, but these agents also have potential liabilities which include osteomalacia, extremely long half-life in bone (greater than 2 years), and possible "frozen bone syndrome" (e.g., the cessation of normal bone remodeling).

Senile Osteoporosis

Senile osteoporosis is similar to postmenopausal osteoporosis in that it is marked by the loss on bone mineral density and resulting increase in fracture rate, morbidity, and associated mortality. Generally, it occurs in later life, 70+ years. Although, in the past, it has been more common in females, with the advent of a more elderly male population, this disease is becoming a major factor in the health of both sexes. It is not clear what, if any, the role of hormones such as testosterone or estrogen have in this disease, and its etiology remains obscure.

Treatment of this disease has not been very satisfactory and there presently are no drugs approved for the treatment of senile osteoporosis. Hormone therapy, estrogen in women and testosterone men have shown equivocal results. Calcitonin and bis-phosphonates may be of some utility and are undergoing clinical evaluation at the present time, but none have been approved in the United States for this use.

An agent which would inhibit bone loss and, thus, retain bone mineral density and structural integrity of the skeleton, would be of great medical benefit.

Vanadium is a transition metal, element 23, and a member of the Vb elements. It is commonly found in a number of oxidation states including the (V) state (e.g., vanadate, sodium orthovanadate, and sodium metavanadate), and the (IV) state (vanadyl, including, for example, vanadyl sulfate). Vanadium has been considered to be an essential trace element for mammalian systems. However, its exact function, especially in humans, is unknown [see, e.g., Nielsen, F. H., *Fed. Proc.,* 5: 123–132 (1986)].

More recently, there has been renewed interest in the pharmacology of Vanadium compounds in the area of glucose regulation, diabetes, and some forms of hypertension. The activity of orthovanadate in diabetes was reveiwed by Heyliger, C. E., et al., in *Science,* 227:1474–1477 (1985). It also has been discovered that vanadium (IV), specifically vanadyl sulfate, is effective in the treatment of experimental diabetes [see, Ramanadham, S., et al., *Am. J. of Physiology,* 257:H904–H911], certain chelates of vanadium (IV) are effective in treating experimental models of diabetes [see, e.g., Dai, S., et al., *Pharmacology Comm.,* 3(4):311–321 (1993) and PCT WO 93/06811]. Dai, et al., also have disclosed that the vanadium (IV) compounds are less toxic and better absorbed via the oral route than either vanadate or vanadyl sulfate [Dai, S., et al., *Pharmac. & Toxicol.,* 75:265–273 (1994)].

SUMMARY OF THE INVENTION

It now has been discovered that certain vanadium (IV) chelates, and pharmaceutically acceptable solvates and hydrates thereof, are effective for inhibiting bone loss in humans. Accordingly, the present invention provides methods for inhibiting bone loss comprising administering to a human in need of treatment an effective amount of a compound of formula I.

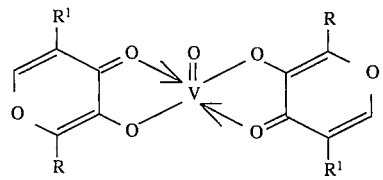

wherein
each R is the same or different —H, —$C_1$-$C_6$ alkyl, —$CH_2OH$, or —$CH_2O$ ($C_1$-$C_6$) alkyl; and
each $R^1$ is the same or different —H, —$C_1$-$C_6$ alkyl, —$CH_2OH$, or —$CH_2O$ ($C_1$-$C_6$)alkyl;
or a pharmaceutically acceptable solvate or hydrate thereof.

The inhibition of bone loss contemplated by the present methods includes both medical therapeutic and/or prophylactic treatment, as appropriate. Thus, a "patient in need of treatment" contemplates an individual who is suffering from bone loss as well as one who is at risk of future bone loss.

The present invention also provides pharmaceutical compositions comprising a compound of formula I, or a pharmaceutically acceptable solvate or hydrate thereof, together with a pharmaceutically accepted carrier, diluent, or excipient.

DETAILED DESCRIPTION OF THE INVENTION

As used herein, the general chemical terms used in the description of compounds of formula I have their usual meanings. For example, the term "—$C_1$-$C_6$ alkyl" includes straight or branched alkyl groups of 1–6 carbon atoms and include, for example, methyl, ethyl, propyl, isopropyl, tert-butyl, and the like.

In using the methods of the present invention, preferred formula I compounds are those in which each R is methyl and each $R^1$ is hydrogen, or each R is hydrogen and each $R^1$ is —$CH_2OH$.

Preparation of compounds of formula I are well known to those of ordinary skill in the art. The preferred compounds of formula I are specifically revealed in the PCT publication WO 93/08611; and McNeill, J. H., et al., *J. Med. Chem.,* 32(8):1489–1492 (1992). The following Examples further explain the preparation and use of compounds of formula I for the methods of the present invention.

Example 1

Bis-(3-hydroxy-2-methyl-4-pyrone)oxovanadium (IV)

A solution of vanadyl sulfate (Aldrich Chem. Co., Milwaukee, Wisc.) and 3-hydroxy-2-methyl-4-pyrone (maltol) in a molar ratio of one to two was prepared in hot water. The solution was raised to a pH of 8.5 with 1N sodium hydroxide. The solution was allowed to reflux for sixteen hours. The reaction mixture was then allowed to cool to ambient temperature. The product was filtered off and dried. This yielded the title compound as purple-green solid.

PMR: ($D^4$ MeOH) consistent with the proposed structure.
MS: m/e=317 (M+) EI
EA: Calc: C, 45.45; H, 3.18 Found: C, 45.60; H, 3.30.

Example 2

Bis-(3-hydroxy-5-hydroxymethyl-4-pyrone)oxovanadium (IV)

A solution was prepared by dissolving 2.5 g (9.88 mmol) of vanadium (IV) sulfate pentahydrate (Aldrich Chem. Co.) in 10 mL of hot water. The solution was degassed with argon for 10 minutes and added to a solution of 2.88 g (20.3 mmol) of 3-hydroxy-5-hydroxymethyl-4-pyrone (kojic acid) in 10 mL of water. To the reaction mixture was added 2.97 g (21.8 mmol) of sodium acetate trihydrate and degassed with argon. The reaction mixture was refluxed under an argon atmosphere for sixteen hours. The reaction mixture was allowed to cool to ambient temperature, and the product was filtered and dried. This yielded 2.69 g of the title compound as a blue solid.

MS: m/e=350 (M+1)
EA: Calc: C, 41.28; H, 2.89 Found: C, 41.06; H, 2.89
IR: (KBr) 1610, 1550, 1500, and 1470 $cm^{-1}$.

The administration of compounds of formula I, in order to practice the present methods of therapy, is carried out by administering an effective amount of the chosen compound to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment. Accordingly, a typical daily dose of a compound of formula I is in the range from about 50 mg to about 1000 mg per day. More preferred ranges of daily dosage are from about 50 mg to about 500 mg per day, and, more particularly, from about 75 mg to about 150 mg per day. The compounds may be administered in a single daily dose, or the daily dose may be administered in portions at intervals throughout the day, as is preferred in the judgment of the physician. It may be deemed advisable by the attending physician that this course of therapy may be continuous or, if warranted, such therapy may be cyclic.

Test Procedures

Inhibition Of Bone Loss I

In the examples illustrating the methods of this invention, a model of postmenopausal osteoporosis is used in which the effects on femoral density of different treatments can be determined.

Seventy-five day old female Sprague Dawley rats (weight range of 225 to 275 g) are obtained from Charles River Laboratories (Portage, Mich.). They are housed in groups of three and had ad libitum access to food (calcium content approximately 1%) and water. Ambient temperature is maintained at 22°–24 C. with a relative humidity of 40%. The photo-period in the room is 12 hours of light and 12 hours of darkness.

One week after arrival, the rats undergo bilateral ovariectomy under anesthesia (44 mg/kg Ketamine® and 5 mg/kg Xylazine®; Butler Chemical Co., Indianapolis, Ind.) administered intramuscularly. Treatment with the vehicle (0.5 mL of 1% caboxymethyl cellulose (CMC) by oral gavage) as the negative control, and treatment with 17β-ethynyl-17-α-hydroxyestradiol (100 µg/kg in 1% CMC via oral gavage) as the positive control, is initiated on the day of surgery following recovery from the anesthesia. A base control of sham operated rats are maintained under the same conditions during the experiment. A compound of formula I is administered by dissolving the compound in the drinking water of the animals. An escalation of dose of the test compound is described in Dia, S., et al., supra, beginning with a dose of 0.5 mg/mL and raising it to 1.25 mg/mL.

The animals are treated for 35 days (6 rats per test group) and sacrificed by decapitation on the 36th day. The 35 day period is sufficient to allow maximal reduction in bone density. The right femurs are excised and scanned at the distal metaphysis 1 mm from the patellar groove with single photon absorptiometry. Results of the densitometer measurements are represented as calculation of the bone mineral content and bone width. Comparisons are then calculated between the various groups.

Inhibition of Bone Loss II

Postmenopausal Osteoporosis

Fracture rate as a consequence of osteoporosis is inversely correlated with bone mineral density. However, changes in bone density occur slowly, and are meaningful only after many months or years. It is possible, however, to demonstrate that a compound of Formula I has positive effects on bone mineral density and bone loss by measuring various quickly responding biochemical parameters that reflect changes in skeletal metabolism. Therefore, two types of clinical evaluation are used to demonstrate the efficacy of compounds of the present invention: 1) a 6–12 month trial is useful for demonstrating the positive effects via biochemical parameters, and 2) 2–4 year trial is useful for demonstrating the positive effects via parameters such as fracture rate.

One hundred, healthy postmenopausal women (natural or surgical), age 45–55, who would normally be considered for estrogen replacement, calcitonin, bis-phosphonate, or antiestrogen therapy for the treatment of osteoporosis, are selected for this clinical evaluation. This would include women who have had their last menstrual period more than six months, but less than six years, in the past.

Patients who have received any of the following medications systematically prior to the study would be excluded from the study: vitamin D, corticosteroids, hypolipidemics, thiazides, antigout agents, salicylates, phenothiazines, sulfonates, tetracyclines, neomycin, or antihelmintics. Patients who have received any estrogen, progestin, or androgen therapy less than six months prior to the initiation of the study, would be excluded. Additionally, any patients who have ever received calcitonin, fluoride, or bis-phosphonates, would be excluded from the study.

The study would be double-blind in design, in that neither the patients nor the investigators would know to which treatment group a patient would be assigned.

There are two groups of fifty patients each. The treatment group receives from about 50 to about 1000 mg per day of an orally administered compound of formula I. The second group receives a placebo.

A baseline examination of each patient would include quantitative measurements of urinary calcium, creatinine, hydroxyproline, and pyridinol crosslinks. Blood samples are measured for osteocalcin and bone-specific alkaline phosphatase.

During subsequent visits (every 3 months in the short-term study and every 6 months in the longer-term studies) to the investigating physician, measurements of the above parameters are made to determine the patient's response to the treatment. All of the biochemical markers listed above are associated with bone resorption and are known to respond to agents effective in the treatment of postmenopausal osteoporosis.

In longer-term studies (greater than 2 years), the same protocols, exclusions, treatments, and measurements as above are made with the addition of measuring the change in bone mineral density from the initial baseline at each periodic visit and at the final end-point. The bone mineral density is measured by either single photon or dual energy X-ray absroptiometry (DEXA) of the femur or tibia. Also, the fracture rate of the two groups is compared.

Inhibition Of Bone Loss III

Senile osteoporosis

A clinical investigation demonstrating the utility of this invention in treating senile osteoporosis is essentially of the same design to outlined above. Both short- and long-term studies are used. In the present study, both men and women would be included, and median age of the patient is between 70–80 years.

Another aspect of the present invention provides pharmaceutical compositions comprising a compound of formula I, or a pharmaceutically acceptable solvate or hydrate thereof, together with a pharmaceutically acceptable carrier, diluent, or excipient. Pharmaceutical formulations are prepared by procedures well known in the art. For example, the compounds can be formulated with common excipients, diluents, or carriers, and formed into tablets, powders, capsules and the like. Examples of excipients, diluents, and carriers that are suitable for such formulations include the following: fillers and extenders such as starch, sugars, mannitol, and silicic derivatives; binding agents such as caboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate and solid polyethyl glycols. Final pharmaceutical forms may be: pills, tablets, powders, lozenges, syrups, saches, cachets, elixirs, suspensions, emulsions, suppositories, or sterile packaged powders, depending on the type of excipient used.

Additionally, compounds of formula I are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

Formulation 1

Hard gelatin capsules are prepared using the following ingredients.

|  | Quantity (mg/capsule) |
| --- | --- |
| Active ingredient | 100 |
| Starch, dried | 400 |
| Magnesium stearate | 10 |
| Total | 510 mg |

Formulation 2

A tablet is prepared using the ingredients below:

|  | Quantity (mg/capsule) |
| --- | --- |
| Active ingredient | 100 |
| Cellulose, microcrystalline | 600 |
| Silicon dioxide, fumed | 10 |
| Stearate acid | 5 |
| Total | 715 mg |

The components are blended and compressed to form tablets each weighing 715 mg.

| Active ingredient | 100 mg |
| --- | --- |
| Starch | 70 mg |
| Microcrystalline cellulose | 60 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 240 mg |

The active ingredient, starch and cellulose are passed through a No. 45 mesh U.S. sieve and mixed thoroughly. The aqueous solution containing polyvinyl - pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 240 mg.

Formulation 4

Capsules, each containing 100 mg of active ingredient, are made as follows:

| Active ingredient | 100 mg |
| --- | --- |
| Starch | 58 mg |
| Microcrystalline cellulose | 58 mg |
| Magnesium stearate | 4 mg |
| Total | 220 mg |

The active ingredient, cellulose, starch, and magnesium stearate are blended, passed through a No. 45 mesh U.S. sieve, and filled into hard gelatin capsules in 220 mg quantities.

Formulation 5

Suppositories, each containing 100 mg of active ingredient per dose, are made as follows:

| Active ingredient | 100 mg |
| --- | --- |
| Saturated fatty acid glycerid | 2,000 mg |
| Total | 2,100 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 6

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 7

An intravenous formulation may be prepared as follows:

| Active ingredient | 10 mg |
|---|---|
| Isotonic saline | 1,000 ml |

The solution of the above ingredients generally is administered intravenously to a subject at a rate of 1 ml per minute.

I claim:

1. A method for inhibiting bone loss comprising administering to a human in need of treatment an effective amount of a compound of formula I

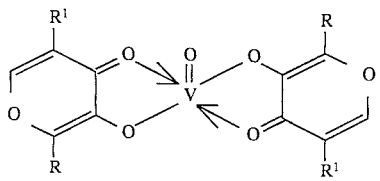

wherein each R is the same or different —H, —$C_1$-$C_6$ alkyl, —$CH_2OH$, or —$CH_2O(C_1$-$C_6)$ alkyl; and each $R^1$ is the same or different —H, —$C_1$-$C_6$ alkyl, —$CH_2OH$, or —$CH_2O(C_1$-$C_6)$alkyl;

or a pharmaceutically acceptable solvate or hydrate thereof.

2. A method according to claim 1 wherein each R is methyl and each $R^1$ is hydrogen.

3. A method according to claim 2 wherein said bone loss is osteoporosis.

4. A method according to claim 3 wherein said osteoporosis is postmenopausal osteoporosis and said human is a female.

5. A method according to claim 3 wherein said osteoporosis is senile osteoporosis.

6. A method according to claim 5 wherein said human is a female.

7. A method according to claim 1 wherein each R is hydrogen and each $R^1$ is —$CH_2OH$.

8. A method according to claim 7 wherein said bone loss is osteoporosis.

9. A method according to claim 8 wherein said osteoporosis is postmenopausal osteoporosis and said human is a female.

10. A method according to claim 8 wherein said osteoporosis is senile osteoporosis.

11. A method according to claim 10 wherein said human is a female.

* * * * *